(12) United States Patent
Chang

(10) Patent No.: US 6,408,853 B1
(45) Date of Patent: Jun. 25, 2002

(54) MEDICAL FACEMASK AND A MOLD FOR MANUFACTURING THE MEDICAL FACEMASK

(76) Inventor: Ti-Li Chang, No. 6, Lane 90, Shen-Lin Rd., Shen-Kang Hsiang, Taichung Hsien (TW)

( * ) Notice: Subject to any disclaimer, the term of this patent is extended or adjusted under 35 U.S.C. 154(b) by 0 days.

(21) Appl. No.: 09/891,468

(22) Filed: Jun. 27, 2001

(51) Int. Cl.$^7$ .................................................. A61F 11/00
(52) U.S. Cl. ................................. 128/857; 128/203.29
(58) Field of Search .............................. 128/848, 857, 128/858, 859, 200.26, 202.28, 203.29, 205.25, 206.21, 206.28

(56) References Cited

U.S. PATENT DOCUMENTS

| | | | | |
|---|---|---|---|---|
| 2,254,854 A | * | 9/1941 | O'Connell | 128/206.25 |
| 4,580,556 A | * | 4/1986 | Kundur | 128/206.28 |
| 4,848,331 A | * | 7/1989 | Northway-Meyer | 128/205.12 |
| 5,676,133 A | * | 10/1997 | Hickie | 128/202.27 |

\* cited by examiner

Primary Examiner—Michael A. Brown
(74) Attorney, Agent, or Firm—Rabin & Berdo, P.C.

(57) ABSTRACT

A medical facemask includes an air cushion to form a seal around a patient's mouth and nose. The air cushion has a facing side contacting the patient's face. The facing side of the air cushion is soft and thin. The facing side has a thickness between 0.15–0.2 mm. The mold for manufacturing the medical facemask includes two mold blocks abutting each other and each having a cavity defined to correspond to each other. An inlet is defined and communicates with one end of the cavity where a nose portion of the medical facemask is formed. The two mold blocks each has multiple outlets defined to communicate with the cavity. To form a thinner facing side, the diameter of the outlets of the mold block forming the facing side is two to five time greater than that of the outlets in the other mold block.

6 Claims, 7 Drawing Sheets

MEDICAL FACEMASK AND A MOLD FOR MANUFACTURING THE MEDICAL FACEMASK

BACKGROUND OF THE INVENTION

1. Field of the Invention

The present invention relates to a medical facemask, and more particularly to a medical facemask and the mold for manufacturing the medical facemask.

2. Description of Related Art

With reference to FIGS. 5 and 6, a conventional medical facemask in accordance with the prior art comprises a shell (50) and an air cushion (60) securely attached to the shell (50). The air cushion (60) covers a patient's mouth and nose. The air cushion (60) has a first end (62) in contact with a patient's chin and a second end (61) covering the bridge of the patient's nose. A gas such as oxygen or anaesthetic flows into the shell (50) for the patient to breathe.

The air cushion (60) is a bladder-like structure with a thickness of about 0.3 mm, and the surface of the air cushion (60) is slick. A thick air cushion (60) may initiate a claustrophobic response in the patient due to the weight of the mask, and the slick surface of the air cushion (60) will stick to the patient's face due to the perspiration. The conventional mask is very uncomfortable.

The disadvantages preciously mentioned are caused by the mold used to manufacture the conventional medical facemask. With reference to FIGS. 5, 7 and 8, the mold for manufacturing the conventional medical facemask is a blowing mold (70) and includes two mold blocks (71) abutting each other. Each of the mold blocks (71) has a cavity (72) defined to correspond to the other cavity (72). An inlet (73) is defined between the two mold blocks (71) and communicates with the cavity (72) where the mold (70) forms the first end (62) of the conventional medical facemask. The two mold blocks (71) respectively include multiple outlets (74) defined to communicate with the cavity (72).

To form the conventional facemask, a piece of hollow material is put into the inlet (73). High-pressure air is blown into the mold, and the original air in the cavity (72) is forced out of the mold through the outlets (74). Then the hollow material stretches to abut the periphery of the cavity (72) to form the air cushion (60), and a joint line (601) is formed on the air cushion (60) at the joint between the two blocks (71).

The joint line (601) of the conventional medical facemask is formed on the middle portion of the air cushion (60) so that the thickness of the air cushion (60) is equal everywhere and about 0.3 mm. The thick air cushion (60) may make the patient feel heavy and uncomfortable.

The present invention has arisen to mitigate and/or obviate the disadvantages of the conventional medical facemask and the mold for manufacturing the conventional medical facemask.

SUMMARY OF THE INVENTION

The main objective of the present invention is to provide an improved a medical facemask and a mold for manufacturing the medical facemask. To achieve the objective, the medical facemask in accordance with the present invention includes an air cushion to fit around a patient's mouth and nose. The air cushion has a facing side to contact the patient's face. The facing side of the air cushion is soft and thin. The facing side has a thickness between 0.15–0.2 mm and forms a textured surface to abut the patient's face to prevent the medical facemask from sticking to the patient's face due to perspiration.

The mold for manufacturing the medical facemask in accordance with the present invention includes two mold blocks abutting each other. Each mold block has a mold face, a top, a bottom, a cavity, an inlet and multiple outlets. The cavity is defined perpendicular to the mold face such that the cavity in one mold block corresponds to the cavity in the other mold block. An inlet is defined in the top of the mold and communicates with one end of the cavity corresponding to portion of the medical facemask that covers a patient's nose. Each mold blocks has multiple outlets defined to communicate with the cavity. To form a thinner facing side, the outlets in the mold block forming the facing side have diameters two to five times larger than the diameters of the outlets in the other mold block. A recess is defined in the face of the first cavity to receive a fine mesh net to form a contact surface and prevent the material from flowing into the first outlet during the formation of the medical facemask.

Further benefits and advantages of the present invention will become apparent after a careful reading of the detailed description with appropriate reference to the accompanying drawings.

DETAILED DESCRIPTION OF THE INVENTION

Figure 1:
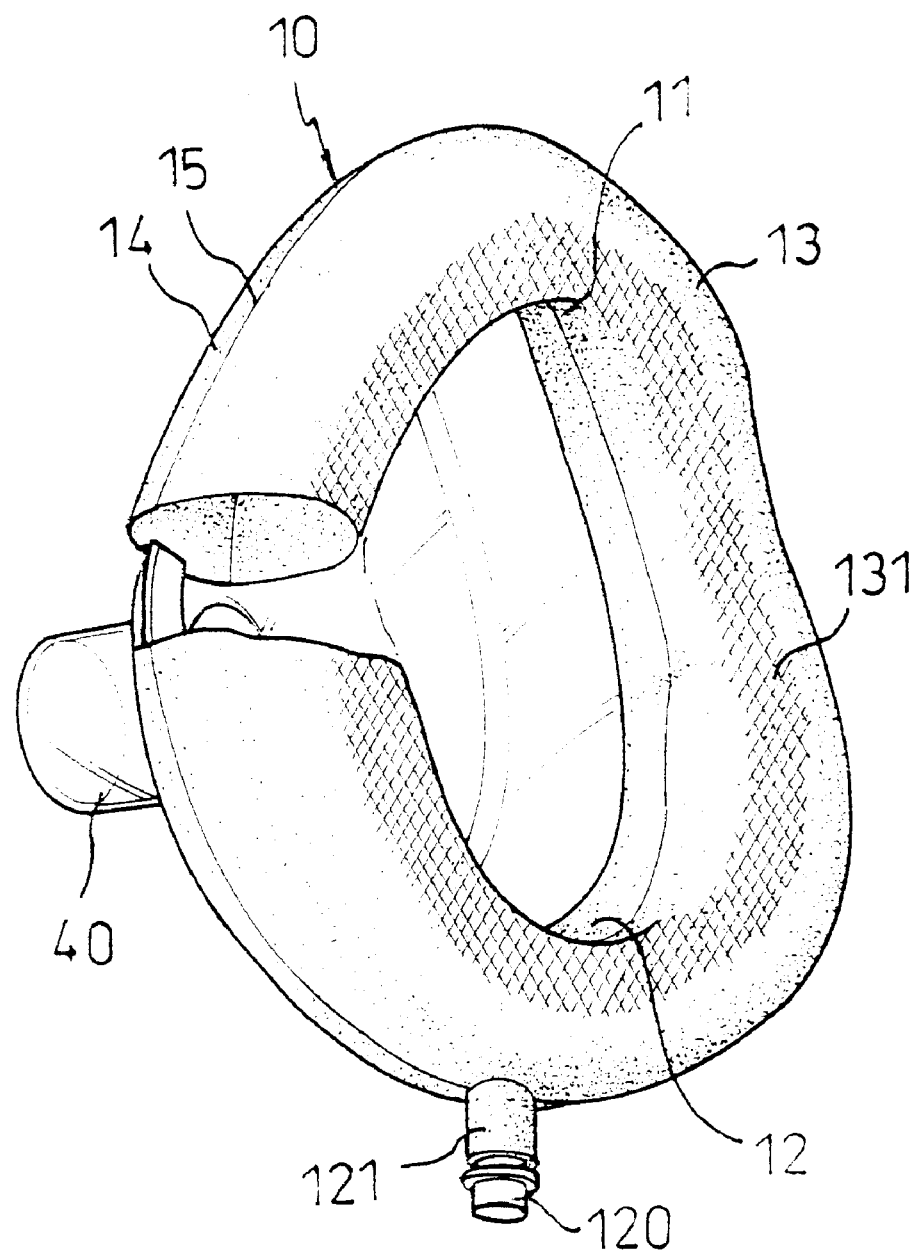
FIG. 1 is a perspective view of a medical facemask in accordance with the present invention.

With reference to the drawings and initially to FIG. 1, a medical facemask in accordance with the present invention comprises a shell (40) and an air cushion (10). The shell (40) has a concave facing side (not numbered) and an exterior side (not numbered). The exterior side of the shell (40) is adapted to connect to an air source, and the air cushion (10) is a flexible, non-permeable material (not numbered) and is attached to the facing side of the shell (40) with an airtight fit. The air cushion (10) includes a nose portion (11) to fit around a user's nose, a mouth portion (12) to fit around the user's mouth and a nipple (121) to inflate or deflate the air cushion (10). The air cushion (10) comprises a hollow inside and an outside surface comprising a facing side (13) to press against the user's face and a connecting side (14) securely joined with the facing side (13) and connected to the shell (40). The nipple (121) is integrally formed with and extends outward from the mouth portion (12) of the air cushion (10) and communicates with the inside of the air cushion (10). A check valve (120) is securely received in the nipple (121) of the air cushion (10) so that air can be pumped into the air cushion (10). The connecting side (14) is formed parallel with the facing side (13), and a joint line (15) is formed at the joint between the facing side (13) and the connecting side (14). The facing side (13) has a textured surface (131) formed to press against a user's face to prevent the medical facemask from sticking to or slipping off the user's face. The facing side (13) is half as thick as the connecting side (14) so that the facing side (13) is soft and comfortable on the user's face.

Figure 2:
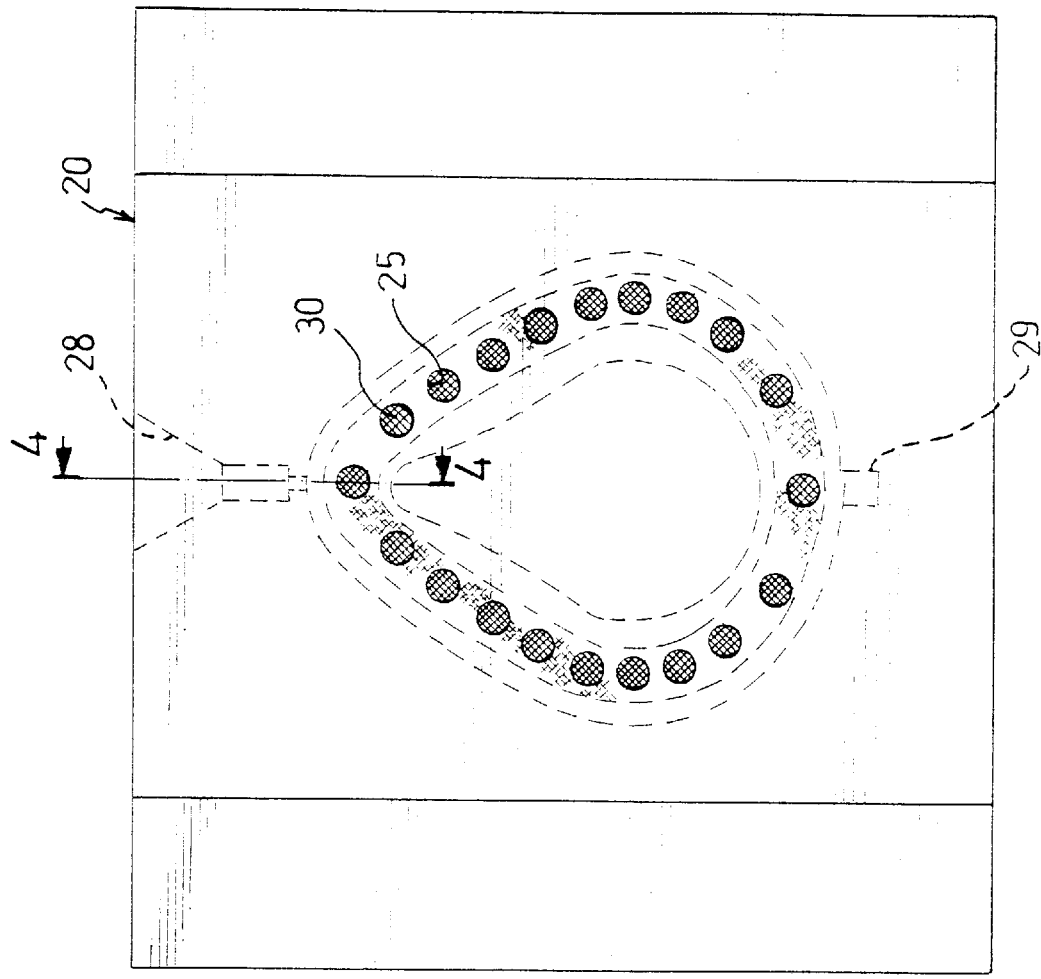
FIG. 2 is a front plan view of a mold in accordance with the present invention for manufacturing the medical facemask in FIG. 1.
Figure 3:
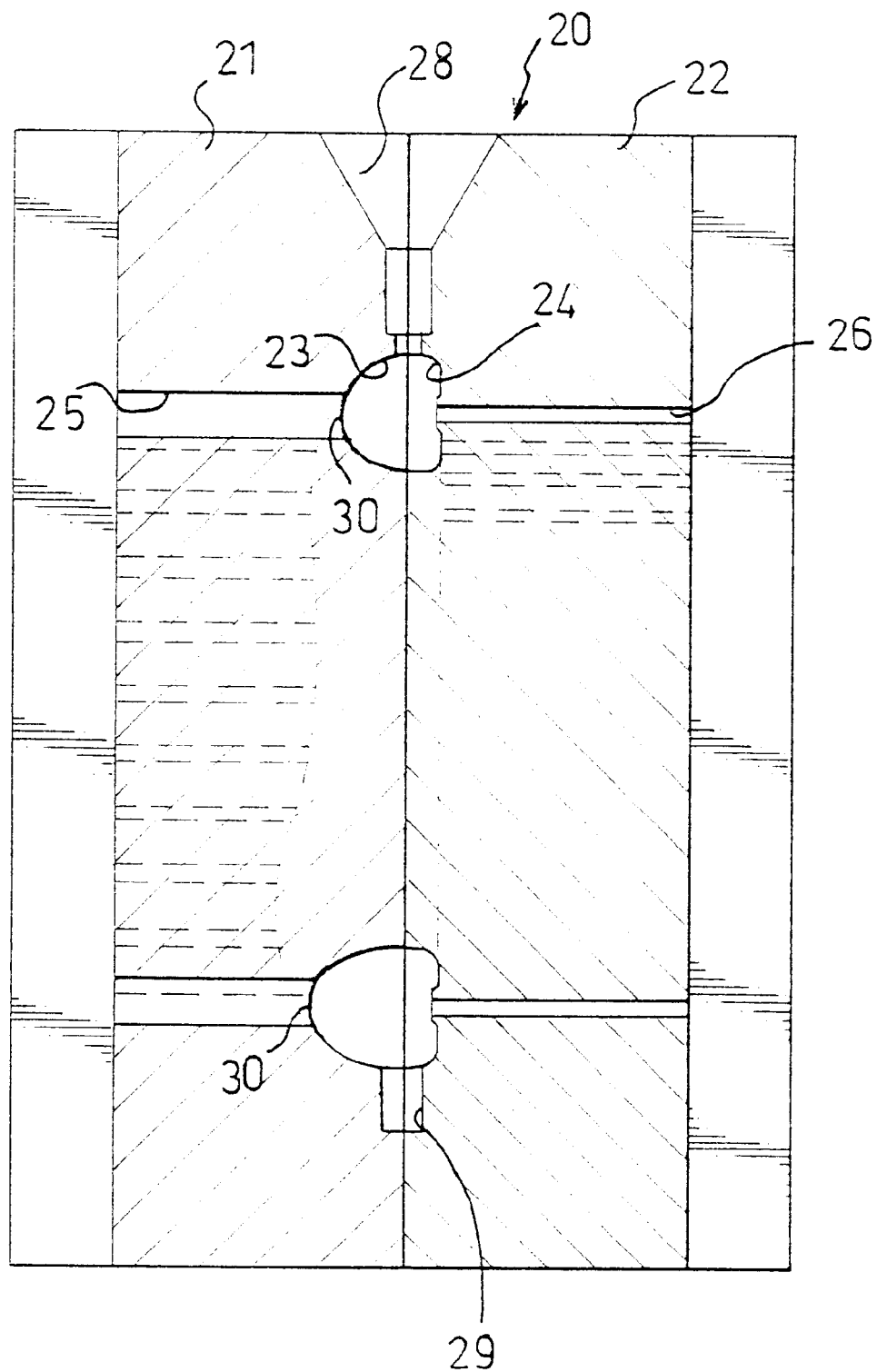
FIG. 3 is a cross sectional side plan view of the mold in FIG. 2 for manufacturing the medical facemask in FIG. 1.

With reference to the FIGS. 2 and 3, the mold (20) for manufacturing the medical facemask in accordance with the present invention comprises a first mold block (21) and a second mold block (22) with a front face, an exterior face, a top, a bottom and two sides. The front faces of the mold blocks (21, 22) abut each other. A first cavity (23) is defined in the front face of the first mold block (21) to form the facing side (13) of the air cushion (10). A second cavity (24) is defined in the front face of the second mold (22) to form the connecting side (14) of the air cushion (10). The first cavity (23) is deeper than the second cavity (24), and the first cavity (23) has a volume greater than that of the second cavity (24). Each of the first cavity (23) and the second cavity (24) has a face (not numbered) and an opening (not numbered) on the front face that correspond to each other. An inlet (28) is defined between the two mold blocks (21, 22) and communicates with the first cavity (23) and the second cavity (24) where the mold forms the nose portion (11) of the air cushion (10). A bore (29) is defined between the two mold blocks (21, 22) opposite the inlet (28) and communicating with the first cavity (23) and the second cavity (24) where the mold forms the mouth portion (12). Multiple first outlets (25) are defined in the first mold block (21) and communicate with the first cavity (23). Multiple second outlets (26) are defined in the second mold block (22) and communicate with the second cavity (24). The diameter of each of the first outlets (25) is two to five times larger than the diameter of each of the second outlets (26).

Figure 4:
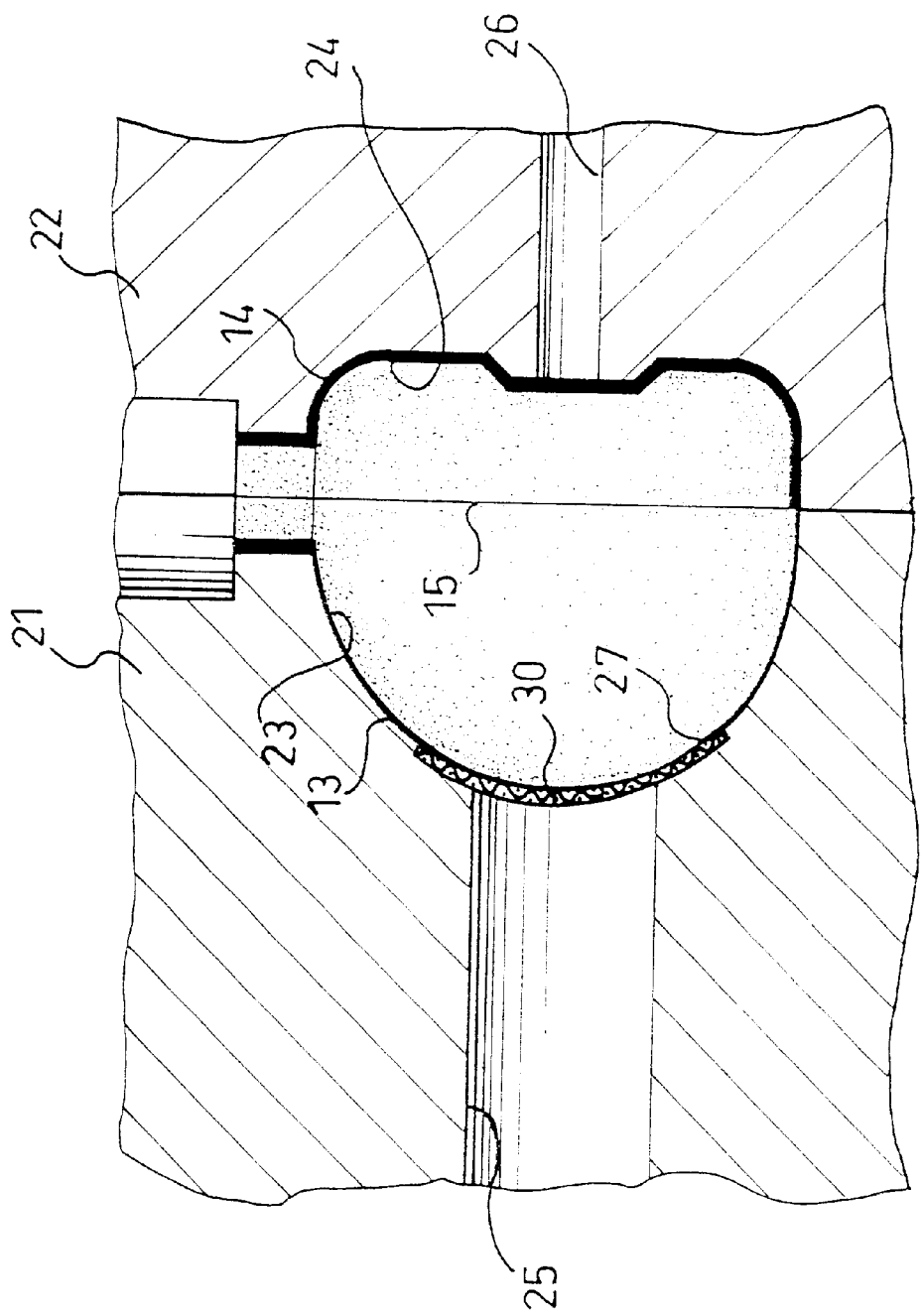
FIG. 4 is an enlarged cross sectional side plan view of the mold along line 4—4 in FIG. 2.
Figure 5:
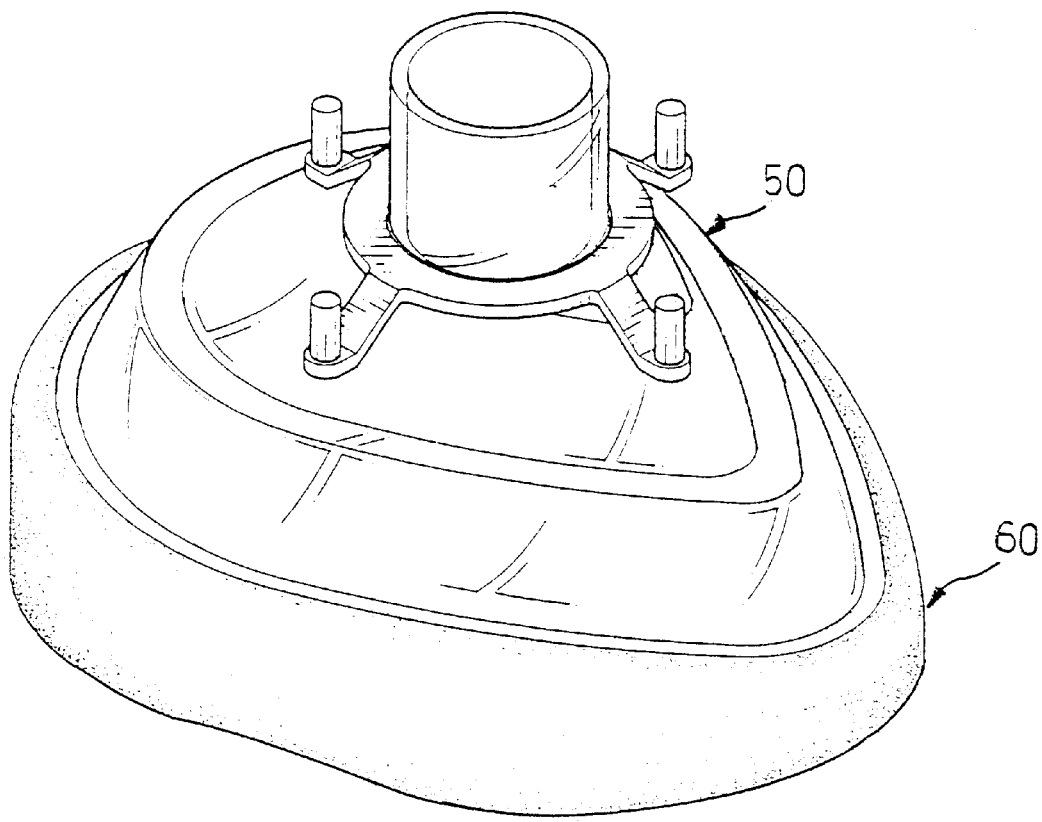
FIG. 5 is a perspective view of a conventional medical facemask in accordance with the prior art.
Figure 6:
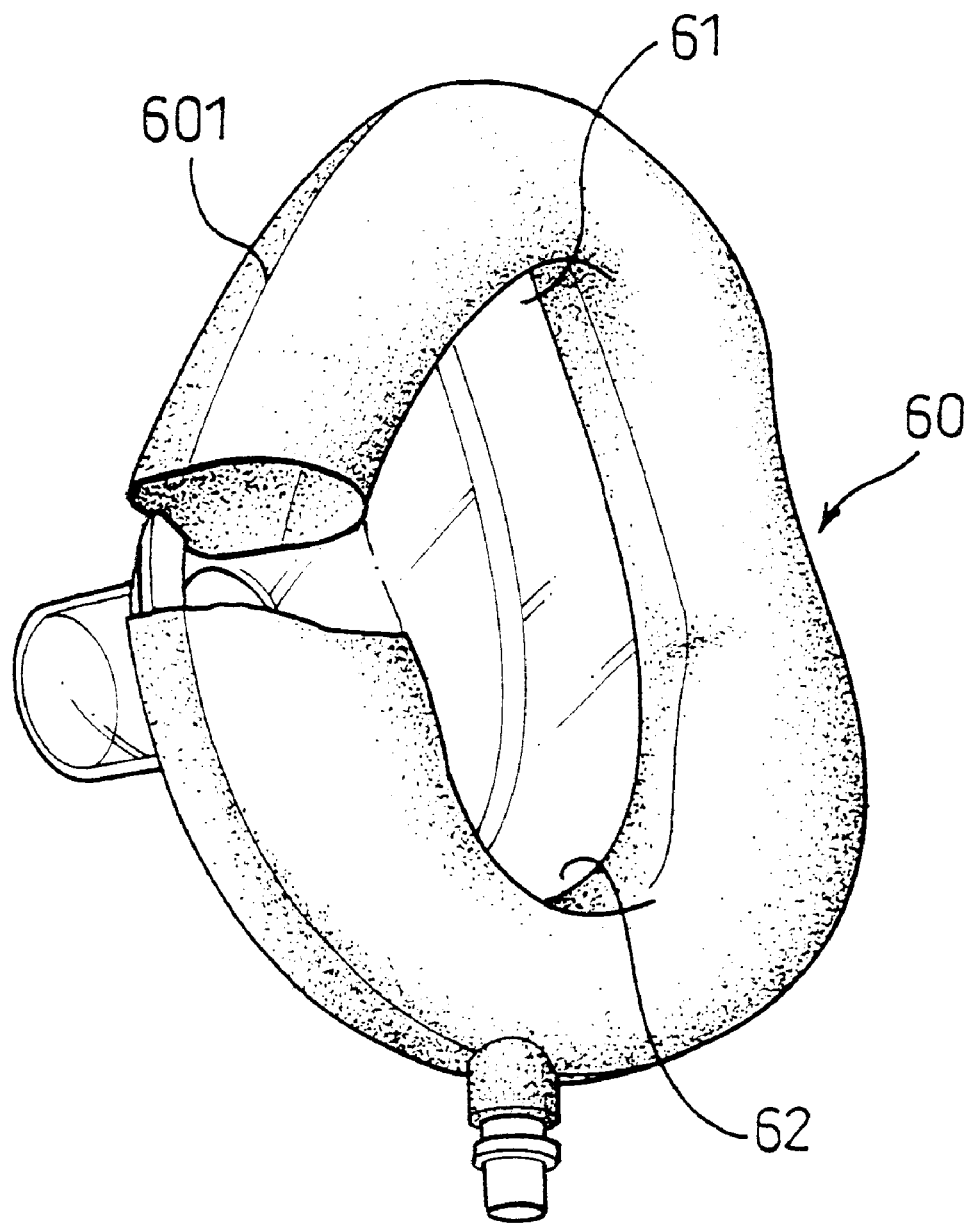
FIG. 6 is a perspective view in partial section of the conventional medical facemask in FIG. 5.
Figure 8:
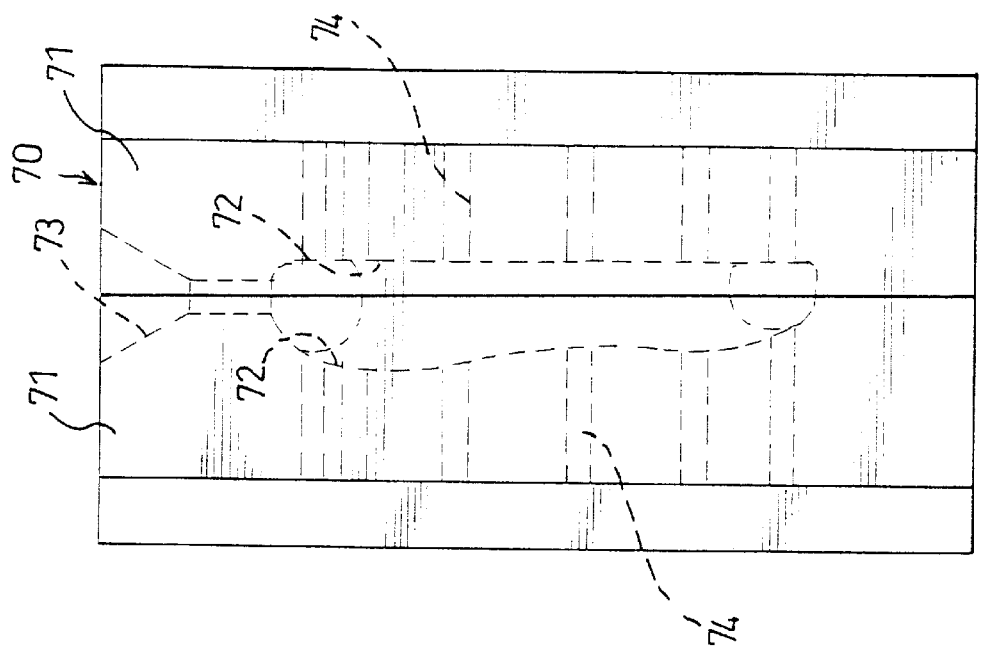
FIG. 8 is a side plan view of the mold for manufacturing the conventional medical facemask in FIG. 5.
Figure 7:
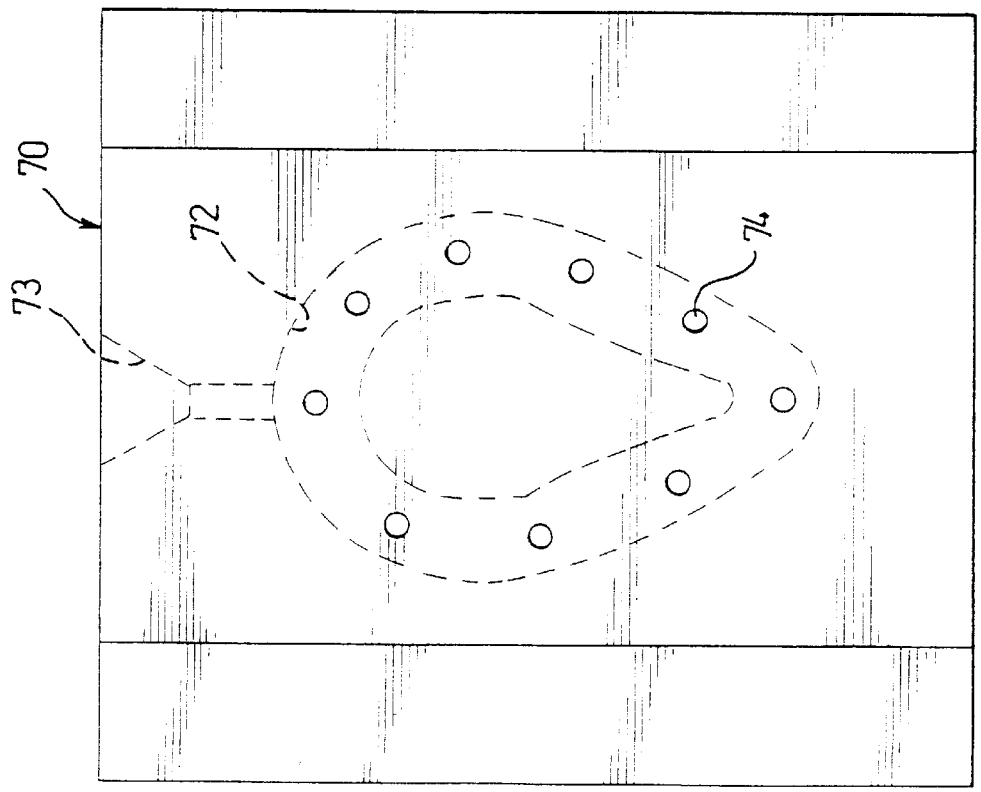
FIG. 7 is a front plan view of the mold for manufacturing the conventional medical facemask in FIG. 5.

With reference to FIG. 4, a recess (27) is defined in the face of the first cavity (23) to receive a fine mesh net (30) to prevent the material from flowing into the first outlet (25) during the formation of the medical facemask. Consequently, the textured surface (131) is formed on the face of the facing side (13). Because the volume of the first cavity (23) is greater than that of the second cavity (24) and the diameter of the first outlet (25) is greater than that of the second outlet (26), the material flow more rapidly on the periphery of the first cavity (23) than the second cavity (24). Consequently, the thickness of the facing side (13) is thinner than that of the connecting side (14). The thinner facing side (13) makes the user feel more comfortable. The thickness of the facing side is between 0.15 to 0.2 mm.

Although the invention has been explained in relation to its preferred embodiment, it is to be understood that many other possible modifications and variations can be made without departing from the spirit and scope of the invention as hereinafter claimed.

What is claimed is:

1. A medical facemask comprising:

a shell adapted to be connected to an air source; and an air cushion attached to the shell with an airtight fit, the air cushion being a bladder structure and including:

a facing side adapted to fit on a user's face around the nose and mouth;

a connecting side attached to the shell, wherein the facing side has a thickness thinner than that of the connecting side;

a nipple integrally outward extending from the air cushion; and a check valve securely received in the nipple so that air can be pumped into the air cushion.

2. The medical facemask as claimed in claim 1, wherein the thickness of the facing side is between 0.15 to 0.2 mm.

3. The medical facemask as claimed in claim 1, wherein the facing side has a textured surface formed and adapted to press against a user's face.

4. The medical facemask as claimed in claim 2, wherein the facing side has a textured surface formed and adapted to press against a user's face.

5. A mold for manufacturing the medical facemask as claimed in claim 1 comprising:

a first mold block having a first cavity defined in the first mold block and multiple first outlets defined to communicate with the first cavity;

a fine mesh net mounted on a bottom of the first cavity and covering the first outlets;

a second mold block abutting the first mold block, the second mold having a second cavity defined to correspond to the first cavity in the first mold block and multiple second outlets defined to communicate with the second cavity;

an inlet defined between the two mold blocks and communicating with the cavity where the mold forms a nose portion of the medical facemask; and a bore defined between the two mold blocks opposite to the inlet and communicating with the cavity where the mold forms a mouth portion of the medical facemask;

wherein the first cavity has a depth deeper than that of the second cavity and the first outlets have a diameter two to five times larger than that of the second outlets.

6. The mold for manufacturing the medical facemask as claimed in claim 5, wherein the first cavity comprises a bottom containing a recess to receive the net.

* * * * *